US009260386B2

(12) United States Patent
Peitz et al.

(10) Patent No.: US 9,260,386 B2
(45) Date of Patent: Feb. 16, 2016

(54) THIOETHERIFICATION OF MERCAPTANES IN C4 HYDROCARBON MIXTURES

(71) Applicants: Stephan Peitz, Oer-Erkenschwick (DE); Markus Winterberg, Waltrop (DE); Dietrich Maschmeyer, Recklinghausen (DE); Frank Geilen, Haltern am See (DE); Reiner Bukohl, Marl (DE); Joerg Schallenberg, Dorsten (DE); Armin Rix, Marl (DE); Andreas Wolff, Recklinghausen (DE); Matthias Leipold, Haltern am See (DE)

(72) Inventors: Stephan Peitz, Oer-Erkenschwick (DE); Markus Winterberg, Waltrop (DE); Dietrich Maschmeyer, Recklinghausen (DE); Frank Geilen, Haltern am See (DE); Reiner Bukohl, Marl (DE); Joerg Schallenberg, Dorsten (DE); Armin Rix, Marl (DE); Andreas Wolff, Recklinghausen (DE); Matthias Leipold, Haltern am See (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/414,540

(22) PCT Filed: Jun. 25, 2013

(86) PCT No.: PCT/EP2013/063300
§ 371 (c)(1),
(2) Date: Jan. 13, 2015

(87) PCT Pub. No.: WO2014/009148
PCT Pub. Date: Jan. 16, 2014

(65) Prior Publication Data
US 2015/0166475 A1    Jun. 18, 2015

(30) Foreign Application Priority Data

Jul. 13, 2012 (DE) .......................... 10 2012 212 317

(51) Int. Cl.
*C07C 319/02*  (2006.01)
*C07C 319/18*  (2006.01)
*C07C 41/06*   (2006.01)

(52) U.S. Cl.
CPC ............... *C07C 319/18* (2013.01); *C07C 41/06* (2013.01)

(58) Field of Classification Search
USPC ................................................. 568/38, 59, 61
See application file for complete search history.

(56) References Cited

U.S. PATENT DOCUMENTS

| 4,695,560 | A  | * | 9/1987  | Gattuso et al. ................. 502/222 |
| 5,338,889 | A  | * | 8/1994  | Vora et al. ..................... 568/697 |
| 5,851,383 | A  | * | 12/1998 | Frey .............................. 208/217 |
| 7,432,407 | B2 |   | 10/2008 | Beckmann et al. |
| 8,197,674 | B2 | * | 6/2012  | Skourlis et al. ............... 208/246 |
| 8,859,834 | B2 |   | 10/2014 | Boeing et al. |
| 2004/0077910 | A1 |   | 4/2004 | Podrebarac et al. |
| 2004/0204614 | A1 |   | 10/2004 | Groten et al. |
| 2005/0010071 | A1 |   | 1/2005 | Podrebarac et al. |
| 2010/0144998 | A1 |   | 6/2010 | Santiago-Fernandez et al. |

FOREIGN PATENT DOCUMENTS

| CN | 101885660 A     | 11/2010 |
| DE | 740 247 C       | 10/1943 |
| DE | 864 866 C       | 1/1953 |
| WO | WO 03/062178 A1 | 7/2003 |
| WO | WO 03/104168 A2 | 12/2003 |
| WO | WO 03/104168 A3 | 12/2003 |
| WO | WO 2014/009159 A2 | 1/2014 |

OTHER PUBLICATIONS

International Search Report issued Nov. 14, 2013 in PCT/EP2013/063300.
Written Opinion issued Mar. 26, 2015 in Singaporean Patent Application No. 11201500169T.

* cited by examiner

*Primary Examiner* — Sudhakar Katakam
*Assistant Examiner* — Pancham Bakshi
(74) *Attorney, Agent, or Firm* — Oblon, McClelland, Maier & Neustadt, L.L.P.

(57) ABSTRACT

The invention relates to a method for the thioetherification of mercaptanes with polyunsaturated hydrocarbons, carried out in a reactor with the addition of hydrogen, using a heterogenic catalyst and in the presence of 1-butene. The aim of the invention is to develop such a method to the extent that the creation of value from the $C_4$ raw material stream is increased. Said aim is achieved in that the hydrogen is added to the reaction in such a manner that the molar ratio of hydrogen to polyunsaturated hydrocarbons is no more than one.

15 Claims, 4 Drawing Sheets

THIOETHERIFICATION OF MERCAPTANES IN C4 HYDROCARBON MIXTURES

CROSS REFERENCE TO RELATED APPLICATIONS

Figure 1:
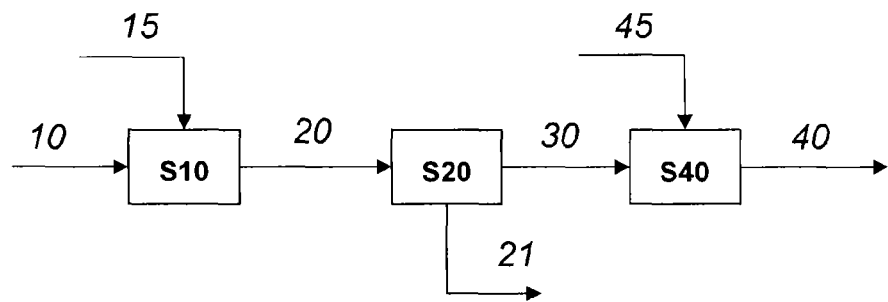

The present application is a 35 U.S.C. §371 national stage patent application of International patent application PCT/EP2013/063300, filed on Jun. 25, 2013, published as WO/2014/009148 on Jan. 16, 2014, the text of which is incorporated by reference, and claims the benefit of the filing date of German application no. 102012212317.2, filed on Jul. 13, 2012, the text of which is also incorporated by reference.

The invention relates to a process for the thioetherification of mercaptans with multiply unsaturated hydrocarbons, carried out in a reactor with addition of hydrogen using a heterogeneous catalyst and in the presence of 1-butene. Such a process is known from U.S. Pat. No. 5,851,383.

$C_4$-Hydrocarbons are compounds which consist exclusively of carbon and hydrogen and in which the number of carbon atoms per molecule is four. Important representatives of $C_4$-hydrocarbons are the alkenes and alkanes having four carbon atoms.

Mixtures of $C_4$-hydrocarbons are raw materials of downstream petrochemistry. They originate either from steam crackers (known as "cracking C4") or from fluid catalytic crackers (known as "FCC C4"). Mixtures of $C_4$ mixtures of various origins are also traded, known as "$C_4$ fraction". For the purposes of utilizing the individual components, the $C_4$ mixtures have to be separated into their constituents, preferably the pure constituents.

Mercaptans are compounds of the class R—SH, where R is an alkyl radical and S is sulphur and H is hydrogen. Mercaptans are also referred to as thiols. Important representatives of mercaptans are methyl mercaptan and ethyl mercaptan, also referred to as methanethiol and ethanethiol, respectively. Mercaptans occur in amounts of up to 1000 ppm as undesirable accompanying materials in $C_4$-hydrocarbon mixtures.

Industrial $C_4$-hydrocarbon mixtures from catalytic crackers (FCC C4) or steam crackers (cracking C4) usually contain not only saturated and monounsaturated compounds but also multiply unsaturated compounds. Before individual compounds can be isolated from these mixtures, it is frequently necessary to remove other compounds as completely as possible. This can be carried out by physical methods, e.g. distillation, extractive distillation or extraction, or else by selective chemical reaction of the components to be removed. Particular attention has to be paid to the very complete removal of the impurities such as oxygen-, nitrogen- and sulphur-containing components present in the $C_4$-hydrocarbon mixture since these can act as catalyst poisons and have adverse effects on the individual process steps. While these impurities are typically present only in traces in cracking C4, they can be present in higher concentrations in FCC C4 streams.

$C_4$-Hydrocarbon mixtures from steam crackers or fluid catalytic crackers typically have the main components shown in Table 1. (Impurities not shown)

TABLE 1

Typical compositions of cracking C4 and FCC C4

| Components | Cracking C4 [% by mass] | FCC C4 [% by mass] |
|---|---|---|
| Isobutane | 1-3 | 20-40 |
| n-Butane | 6-11 | 5-15 |
| 1-Butene | 14-20 | 10-20 |
| 2-Butenes | 4-8 | 20-35 |
| Isobutene | 20-28 | 10-20 |
| 1,3-Butadiene | 40-45 | less than 1 |

The composition of the raw materials can fluctuate greatly depending on the origin of the material. The $C_4$ components indicated are associated with hydrocarbons having fewer or more carbon atoms and also impurities such as mercaptans, sulphides, disulphides, nitrogen- and oxygen-containing compounds in small amounts.

The work-up of FCC C4 can, in one variant, be carried out by firstly reducing the concentration of isobutane by means of a distillation step in a distillation to a value of less than 5% by mass, particularly preferably less than 3% by mass. At the same time, the low boilers (e.g. $C_3$-hydrocarbons, light oxygen-, nitrogen- and sulphur-containing compounds) present in the mixture are removed or minimized. In the subsequent step, all high boilers (e.g. $C_5$-hydrocarbons, heavy oxygen-, nitrogen- and sulphur-containing compounds) are removed at the bottom of a column. In the next step, isobutene is removed, e.g. by reacting it with methanol to form methyl tert-butyl ether (MTBE) and removing the latter by distillation. If pure isobutene is to be obtained, the methyl tert-butyl ether can subsequently be cleaved again to form isobutene and methanol.

To work the $C_4$ mixture up further, the remaining multiply unsaturated compounds have to be converted by means of a selective hydrogenation process into the corresponding monounsaturated and saturated compounds. 1-Butene and remaining isobutane can now be separated off in sufficient purity by distillation and the remaining 2-butenes and n-butane can be worked up further. The 2-butenes are frequently converted by dimerization into octenes which are subsequently converted by means of hydroformylation into PVC plasticizer alcohols. The saturated $C_4$-hydrocarbons can, for example, be used as blowing agents.

If the concentration of the multiply unsaturated compounds is not reduced to a value below 10 ppm in the selective hydrogenation process before the 1-butene is separated off, the purity requirements for 1-butene used in polymerizations are not attained. Furthermore, multiply unsaturated compounds suppress the catalytic activity of the catalysts for the dimerization of 2-butenes.

The work-up of $C_4$ streams from steam crackers or catalytic crackers is described in principle in K.-D. Wiese, F. Nierlich, *DGMK-Tagungsbericht* 2004-3, ISBN 3-936418-23-3.

The demands made of the selectivities in processes for the selective hydrogenation of multiply unsaturated hydrocarbons are particularly great since products of value are destroyed in the case of dehydration, i.e. hydrogenation of monounsaturated compounds, and isomerization of terminal double bonds to internal double bonds. At the same time, in the case of the fine purification of streams which already have a low content of multiply unsaturated compounds, the concentrations of multiply unsaturated compounds have to be reduced further to values below 10 ppmw.

Processes and catalysts for the selective hydrogenation of 1,3-butadiene in high concentration (from about 30 to 50%) in $C_4$ streams are described in EP0523482, DE3119850, EP0992284 and EP0780155.

In the case of catalytic $C_4$ streams, it is possible for not only the light sulphur-containing components which have been separated off by distillation in the low boiler removal, e.g. $H_2S$, COS or MeSH, and the relatively high-boiling sulphur compounds which have been separated off in the $C_5$ column, e.g. dimethyl disulphide, but also mercaptan-type intermediate boilers (e.g. ethanethiol) to be present. These cannot readily be removed by distillation from the $C_4$ stream. The presence of mercaptans is undesirable or interferes in the work-up of $C_4$ streams for a number of reasons:

a) If mercaptans (e.g. ethanethiol) are present in the feed to the selective hydrogenation, these inhibit the catalytic reaction of 1,3-butadiene. Thus, the branched multiply unsaturated compounds can be present in the subsequent product (e.g. 1-butene) and place its purity at risk.

b) If the multiply unsaturated compounds get into the feed for the oligomerization of the n-butenes because of incomplete reaction in the selective hydrogenation due to the mercaptan content, they deactivate the oligomerization catalyst.

c) If the mercaptans get into the feed to the oligomerization of the n-butenes, they deactivate the oligomerization catalyst.

d) It is known that hydroisomerization-active catalysts can be formed by treatment of the selective hydrogenation catalyst with sulphur-containing components. Such a hydroisomerization catalyst which leads to undesirable isomerization of 1-butene to 2-butenes can be formed by the mercaptans present in the feed to the selective hydrogenation.

It is an object of the invention described here to circumvent these problems in the work-up of $C_4$ streams.

As prior art, in the presence of mercaptans it is possible to carry out a process involving extraction of the mercaptans by means of aqueous caustic alkali solution and subsequent oxidative conversion of the mercaptans into disulphides in order to lower the concentration of the mercaptans to values of about 5-15 ppm. Such a process is offered for industrial use by UOP LLC under the name MEROX®. (G. A. Dziabis, "UOP MEROX PROCESS" in Robert Meyers, Handbook of Petroleum Refining Processes, 3rd Edition, 2004 McGraw-Hill).

The disadvantage of the MEROX® process is that it not only requires a high outlay in terms of apparatus but also produces large amounts of water and caustic alkali streams which are costly to dispose of. In addition, complete removal of higher mercaptans (e.g. ethanethiol) is not ensured. It is therefore absolutely necessary to carry out additional measures for removing these residual amounts of mercaptans for further chemical use. This is achieved, for example, by adsorptive removal. Adsorptive processes for the desulphurization of $C_4$ streams are described in DE3914817C2 and DE19845857A1.

As an alternative, processes for the thioetherification of mercaptans with unsaturated hydrocarbons combined with hydrogenation of the multiply unsaturated hydrocarbons and at the same time isomerization of 1-butene to 2-butenes which reduce the concentration of the mercaptans to values below 1 ppm and that of the multiply unsaturated $C_4$-hydrocarbons to values below 10 ppm and also bring the concentration of 1-butene into equilibrium with 2-butene are known.

U.S. Pat. No. 5,851,383 describes such a process for the simultaneous thioetherification of mercaptans to form relatively high-boiling thioethers, selective hydrogenation of multiply unsaturated olefins in FCC $C_3$-$C_5$ streams and isomerization of light monoolefins. The process is carried out in the purely liquid phase in a fixed-bed reactor and nickel on aluminium oxide serves as catalyst. Hydrogen is added in a two-fold molar excess over diolefin.

U.S. Pat. No. 5,463,134 describes a process for the simultaneous acid-catalysed thioetherification of mercaptans with butenes to form relatively high-boiling thioethers and removal of olefins by oligomerization in the absence of hydrogen in a paraffin-rich $C_4$ stream. The process is carried out in the purely liquid phase in a fixed-bed reactor and an acidic ion exchanger serves as catalyst.

WO 2003062178 describes a process for the pretreatment of $C_4$ streams for an alkylation of isobutane by means of butenes. Here, inter alia, a simultaneous thioetherification of mercaptans to form relatively high-boiling thioethers, a selective hydrogenation of multiply unsaturated olefins and isomerization of light monoolefins are carried out. The process is carried out in the purely liquid phase in a fixed-bed reactor and nickel on aluminium oxide serves as catalyst. Hydrogen is added in a ten-fold molar excess over diolefin.

The disadvantage of the thioetherification processes mentioned is that isomerization of 1-olefins, especially 1-butene, takes place in addition to the reaction of the mercaptans and diolefins. This leads to a great decrease in the 1-olefin content, so that subsequent, targeted isolation of the 1-olefins is no longer possible. However, 1-olefins are products of value for which there is demand and can be isolated and utilized to bring a profit.

In WO2003062178 and in U.S. Pat. No. 5,851,383, hydrogenation of the monoolefins also takes place in parallel to the undesirable isomerization as a result of the hydrogen used in a molar excess. This leads to a significant reduction in the total monoolefin content in the product stream, and this is thus no longer available for downstream reactions (e.g. oligomerization).

In the light of this prior art, it is an object of the invention to develop a process of the type mentioned at the outset in such a way that the value derived from the $C_4$ raw material stream used is increased.

This object is achieved by hydrogen being introduced into the reaction in such an amount that the molar ratio of hydrogen to multiply unsaturated hydrocarbons is not more than one.

The invention accordingly provides a process for the thioetherification of mercaptans with multiply unsaturated hydrocarbons, carried out in a reactor with addition of hydrogen using a heterogeneous catalyst and in the presence of 1-butene, in which the molar ratio of hydrogen to multiply unsaturated hydrocarbons is not more than one.

The process of the invention is able to convert mercaptans into high-boiling thioethers with complete conversion, at the same time virtually completely suppress any significant isomerization of 1-butene to internal butenes and also completely prevent hydrogenation of the butenes.

Contrary to the expectations of a person skilled in the art, it is shown in the context of the present invention that mercaptans can be converted in the presence of 1,3-butadiene and hydrogen to below the detection limit into relatively high-boiling thioethers, with the isomerization of 1-butene being greatly suppressed and the hydrogenation of butenes being completely prevented. The detection limit of the mercaptans is at present about 50 ppbw, i.e. a proportion by weight of $50*10^{-9}$.

For the purposes of the present invention, the amount of hydrogen to be adhered to is at the most equimolar relative to the multiply unsaturated hydrocarbons present in the hydrocarbon mixture. The molar ratio of hydrogen to the multiply unsaturated hydrocarbons is preferably in the range from 0.01 to 0.8. It is particularly preferably in the range from 0.1 to 0.5.

A great advantage of this process is that, owing to the low proportion of hydrogen, 1-butene present in the $C_4$ stream is barely isomerized and continues to be available as product of value. In addition, the process makes it possible to dispense with a costly MEROX® scrub. Only the limits to the amount of hydrogen introduced which are to be adhered to precisely make it possible to etherify mercaptans in a process down to concentration values below 50 ppbw by means multiply unsaturated $C_4$-hydrocarbons to form high-boiling thioethers without hydrogenation of the monounsaturated butenes which are likewise present in the feed and appreciable isomerization of 1-butene occurring.

An important characteristic of the process is that no conversion of mercaptans occurs without hydrogen.

The multiply unsaturated hydrocarbons which are thioetherified with the mercaptans are preferably 1,3-butadiene and/or but-3-en-1-yne and/or 1,2-butadiene. These dienes and acetylenes are present in only small amounts, particularly in FCC-C4, and in any case have to be hydrogenated completely downstream and are therefore no longer available as product of value. In the case of cracking C4 streams which have a high 1,3-butadiene content, the 1,3-butadiene is removed separately beforehand and utilized. The residual butadienes remaining in the $C_4$ stream can then be used for the thioethertification.

A particular advantage of the process is that it is reactive not only in respect of the highly reactive mercaptan methanethiol but also in respect of higher mercaptans (e.g. ethanethiol). Thus, the mercaptans methanethiol and/or ethanethiol present in the stream are preferentially thioetherified with multiply unsaturated hydrocarbons.

Carbon monoxide can optionally be additionally added to the hydrocarbon mixture to be hydrogenated. The content of carbon monoxide in the feed is in this case in the range from 0.05 to 20 ppm of carbon monoxide, based on the mass of the hydrocarbon mixture. Preference is given to adding from 0.5 to 5 ppm of carbon monoxide. Added amounts above 20 ppm no longer improve the results. The carbon monoxide is introduced separately into the reactor or added to the inflowing $C_4$ stream.

Carbon monoxide acts as additional moderator which reduces isomerization of 1-butene to 2-butenes.

Suitable catalysts for the thioetherification are heterogeneous catalysts which contain a metal of group VIII of the Periodic Table of the Elements.

In principle, the thioetherification of the invention is not tied to any particular group VIII metal catalyst. The metal is preferably present in supported form on an inert support material. The support material is, for example, aluminium oxide, silica gel or activated carbon. Preference is given to using aluminium oxide as support material.

If the catalyst used is a catalyst based on palladium, it has a palladium concentration in the range from 0.01 to 3%, based on the mass of the support. The concentration is preferably in the range from 0.1 to 1%, very particularly preferably in the range from 0.3 to 0.5%. The catalyst has an internal surface area (determined by gas adsorption in accordance with DIN ISO 9277) of from 50 to 400 m$^2$/g, preferably from 100 to 300 m$^2$/g, particularly preferably from 200 to 300 m$^2$/g.

Coated catalysts which comprise aluminium oxide as support and palladium as catalytically active metal have been found to be particularly advantageous for the thioetherification.

The entry temperature of the reactor feed is preferably in the range from 0 to 180° C., more preferably in the range from 60 to 150° C., particularly preferably in the range from 80 to 130° C. The pressure is preferably in the range from 0.2 to 5 MPa, more preferably in the range from 0.6 to 4 MPa, particularly preferably in the range from 1 to 3 MPa. In all cases, the pressure has to be selected so that the hydrogen remains completely dissolved and no gas phase occurs in the reactor.

The thioetherification is preferably operated as a liquid-phase process. This means that all components are present in the liquid phase over the catalyst or are introduced in liquid form into the reactor. In particular, it means that the hydrogen and optionally also the carbon monoxide are completely dissolved in the liquid phase.

The addition of hydrogen to the mixture of hydrocarbons to be hydrogenated is thus effected in finely divided form and in such amounts that a homogeneous liquid phase is always present before entry into the hydrogenation reactor.

The hydrocarbon mixtures to be etherified can contain up to 1000 wppm of mercaptans, i.e. a proportion by weight of $10^{-3}$. The thioetherification can be carried out in one or more reaction stages. If the amount of mercaptans present in the feed is so great that the amount of hydrogen required is no longer soluble in the feed, the feed can be diluted by means of a recycle mode of operation. As an alternative, the hydrogen can be added in a plurality of partial amounts distributed over the length of the reactor or over the individual reaction stages.

After complete conversion of the mercaptans into high-boiling thioethers, these thioethers can be separated off by distillation. This reduces the thioether content of the remaining $C_4$-hydrocarbon mixture to below 50 ppbw. Together with a possible low boiler removal upstream of the thioetherification reactor and a high boiler distillation downstream of the thioetherification reactor, complete removal of all sulphur-containing components from the $C_4$-hydrocarbon mixture is thus possible.

The concentration of multiply unsaturated olefins can be measured on-line by means of gas chromatography and the amount of hydrogen can be set exactly according thereto. This likewise applies to the sulphur compounds.

The process is preferably applied to mercaptan-containing mixtures of $C_4$-hydrocarbons which originate from catalytic crackers (FCC C4) or from steam crackers (cracking C4). Of course, C4 fraction can also be processed.

The $C_4$-hydrocarbon mixture used as feed is preferably subjected beforehand to a removal of low boilers, in particular isobutane, by distillation.

As an alternative, the process is employed before the removal of isobutane.

After the thioetherification according to the invention, at least one of the following process steps is carried out during the course of the further work-up and utilization of the $C_4$ stream:
　　removal of thioethers by distillation;
　　removal of sulphur components by adsorption;
　　selective hydrogenation of 1,3-butadiene to 1-butene and/
　　　　or 2-butene;
　　removal of 1-butene by distillation;
　　oligomerization of 2-butenes to form olefins having more
　　　　than 4 carbon atoms;
　　removal of n-butane and/or of isobutane by distillation;
　　etherification of isobutene with methanol to form methyl
　　　　tert-butyl ether (MTBE) and removal of the MTBE
　　　　formed.

It is also possible to arrange a number of the processing steps indicated after the thioetherification. The order can be chosen differently depending on the composition of the stream being processed.

In the processing of FCC C4, the following order is particularly preferred:
1. removal of thioethers by distillation;
2. removal of sulphur components by adsorption;
3. etherification of isobutene with methanol to form MTBE and removal of the MTBE formed;
4. selective hydrogenation of 1,3-butadiene to 1-butene and/or 2-butene;
5. removal of 1-butene by distillation;
6. oligomerization of 2-butenes to form olefins having more than 4 carbon atoms.

The removal of thioethers by distillation is customarily effected in a distillation column. At the same time, the high boilers accompanying the $C_4$ stream, e.g. $C_5$-hydrocarbons, are preferably removed together with the thioethers. The desulphurized $C_4$ stream is taken off at the top of the distillation column.

A distillation column which is preferably used in this process step preferably has from 40 to 150 theoretical plates, preferably from 40 to 100 and particularly preferably from 50 to 80 theoretical plates. The reflux ratio is, depending on the number of theoretical plates realised, the composition of the feed to the column and the required purities of distillate and bottom product, preferably in the range from 0.5 to 5, particularly preferably from 1 to 2.5. The reflux ratio is defined here as mass flow of the runback divided by the mass flow of the distillate. The column is preferably operated at an operation pressure of from 0.1 to 2.0 MPa (absolute), preferably from 0.5 to 1.2 MPa (absolute). Heating of the column can be effected using, for example, steam. The condensation can, depending on the operating pressure selected, be effected against cooling brine, cooling water or air. However, the vapour from the top of the column can also be heat-integrated with other columns in the process, e.g. with the column for separating off the isobutane. In this case, the condenser of the column serves simultaneously as vaporizer of the low boiler column. The bottom product can be utilized thermally or be used as starting material for other processes, for example in a synthesis gas plant.

In principle, all mercaptans which are harmful to the catalyst can be removed by means of the thioetherification according to the invention and the subsequent removal of the thioethers formed by distillation. However, since the effects of very small residual amounts of sulphur compounds can cause serious damage in the subsequent process, the removal of sulphur should be designed so as to be redundant. For this purpose, preference is given to providing an adsorber bed through which the overhead stream from the thioether removal by distillation is passed and very small residual amounts of sulphur-containing compounds are adsorbed in the process. In general, the adsorber adsorbs barely any material. In the case of an operational malfunction in the thioetherification or the subsequent distillation, the adsorber also keeps a large burden of sulphur compounds away from downstream catalytic processing steps. Suitable adsorbents for the desulphurization of $C_4$ streams are described in DE3914817C2 or in DE3825169A1 and DE19845857A1.

The adsorptive desulphurization is preferably carried out at a pressure of from 0.1 to 5 MPa and a temperature of from 20 to 160° C. in the liquid phase. Typical trace components which are removed by the purification using the adsorber are, for example, sulphur compounds, nitrogen compounds, oxygen compounds and/or halogen compounds.

In the process of the invention, the isobutene present in the $C_4$ mixture obtained in this way is preferably reacted with methanol over acidic ion exchangers to give an MTBE reaction mixture and the MTBE is separated off from the $C_4$ mixture. In principle, all known processes for the synthesis of MTBE can be used for this purpose; for example, the MTBE synthesis can be carried out in a manner analogous to the description in DE10102082A1.

Remaining butadiene which has not been reacted with the mercaptans to form thioethers is preferably converted selectively into butenes in a hydrogenation step. Since 1,3-butadiene is the most abundant butadiene in $C_4$ streams, it is hydrogenated to 1-butene and/or 2-butene, if possible without hydrogenation of the remaining olefins. The selective hydrogenation of the 1,3-butadiene is particularly preferably carried out at about 40° C. in the liquid phase, at a molar ratio of 1,3-butadiene to hydrogen of 1.1 and with addition of 1 ppm of carbon monoxide over a palladium catalyst. Since these reaction conditions differ significantly from those of the thioetherification, the two steps cannot be carried out in the same reactor. A suitable process for the selective hydrogenation of 1,3-butadiene to 1-butene and/or 2-butenes is disclosed in DE102010030990A1. DE3143647A1 also discloses a suitable process.

The hydrogenation is carried out in the liquid phase over a palladium-containing fixed-bed catalyst using hydrogen with addition of carbon monoxide as moderator. Hydrogen and carbon monoxide are completely dissolved in the hydrocarbon mixture. The amount of hydrogen added is at least the amount which is stoichiometrically required for the hydrogenation of the multiply unsaturated compounds to the monoenes. It can be calculated from the composition of the $C_4$ stream to be hydrogenated.

The amount of CO based on the mass of the $C_4$ stream to be hydrogenated is at least 0.05 ppm. Amounts of above 20 ppm normally do not lead to any further significant improvement in the hydrogenation results, and amounts of from 0.05 to 10 ppm are therefore preferred. The amount of CO which is optimally introduced in the respective process can easily be determined experimentally, as described in DE3143647A1.

The catalyst for the selective hydrogenation comprises from 0.1 to 2% by mass of palladium on a support. Such supports include, for example, aluminium oxide, silica gel, aluminosilicate and activated carbon. The throughput of hydrocarbon per liter of catalyst used is preferably in the range from 5 to 300 liters.

The temperature at which the hydrogenation is carried out is from 0 to 75° C. Very particular preference is given to temperatures of about 40° C.

The process pressure has to be sufficiently high to maintain the liquid phase at the temperature selected and to bring a sufficient amount of hydrogen and carbon monoxide into solution. The reaction pressure is below 20 MPa, preferably below 6 MPa, more preferably below 2 MPa. A typical reaction pressure is 1.5 MPa.

The hydrogenation is preferably carried out in a plurality of stages, particularly preferably two stages. Hydrogen is fed in upstream of each of the reactors, and carbon monoxide is preferably fed into the first of the reactors. The reactors can be operated with recirculation of product.

After the selective hydrogenation, it is possible to separate off the product of value 1-butene. This can be carried out by distillation in one or more distillation columns. In a preferred embodiment, the 1-butene is separated in two distillation columns. In the first distillation column, a fraction rich in isobutane and 1-butene is firstly separated off as overhead product from the C4 mixture, and the stream rich in isobutane and 1-butene is then fractionated in a further distillation column. In this column, very pure 1-butene is obtained as bottom product. An isobutane-rich fraction which may additionally contain low boilers (for example $C_3$-hydrocarbons) is obtained as overhead product.

Pure 1-butene prepared in this work-up step preferably contains less than 5000 ppm by mass, more preferably less than 2000 ppm by mass and particularly preferably less than 1500 ppm by mass, of isobutene and is in demand as an intermediate. It can, for example, be used as comonomer in the preparation of polyethylene (LLDPE or HDPE) and also of ethylene-propylene copolymers. It is also used as alkylating agent and is a starting material for the preparation of 2-butanol, butene oxide, valeraldehyde.

Apart from the 1-butene, isobutane-rich fractions are also obtained in the work-up of the stream by distillation, depending on the starting composition of the $C_4$ hydrocarbons. These isobutane-rich fractions can be purified further, preferably to give pure isobutane. The isobutane obtained in the work-up preferably has a purity of at least 90% by mass of isobutane, particularly preferably 95% by mass of isobutane, and preferably contains less than 1000 wppm, particularly preferably less than 200 wppm, of olefins. Purification to give pure isobutane can, for example, be effected by complete hydrogenation of the alkenes still present to alkanes and subsequent distillation.

Further information on carrying out the 1-butene removal may be found in DE102005062700A1 and DE102005062699A1.

Oligomerizations are particularly susceptible to the catalyst poisons removed in the process of the invention. It is therefore advantageous to subject the $C_4$ stream which has been freed of mercaptans according to the invention to a subsequent oligomerization in the course of which 2-butenes and optionally also remaining 1-butene are oligomerized to form olefins having more than 4 carbon atoms.

In this process step, the butenes are oligomerized over a heterogeneous catalyst comprising nickel, silicon and aluminium to give oligomers. The process underlying this process step is referred to in the literature as OCTOL® process which is described in Hydrocarbon Process., Int. Ed. (1986) 65 (2. Sect. 1), pages 31 to 33, and also in the documents DE3914817, EP1029839 and DE102004018753.

The oligomerization is carried out in the presence of heterogeneous nickel-containing supported catalysts. As support materials, the catalysts can comprise, for example, silicon dioxide and aluminium oxide, aluminosilicates or zeolites. Such catalysts are known in the technical literature and are described, for example, in DE4339713A1 or WO0137989.

The oligomerization is carried out at (reaction) temperatures of from 0 to 200° C., preferably from 50 to 130° C., and pressures of from 0.1 to 70 MPa, preferably from 0.1 to 10 MPa and particularly preferably from 0.5 to 3 MPa.

Oligomers obtained by the oligomerization of the butenes are, in particular, olefins having eight, twelve, sixteen, twenty or more carbon atoms. These olefins can be used, for example, for preparing plasticizer alcohols ($C_9$- or $C_{13}$-alcohols) or alcohols ($C_{13}$-, $C_{17}$- or $C_{21}$-alcohols) for preparing raw materials for laundry detergents. Before further processing, they are preferably worked up by distillation to give one or more fractions, and preferably separated into a fraction comprising dibutenes (mainly $C_8$-olefins), a fraction comprising tributene ($C_{12}$-olefins) and a fraction comprising higher oligomers ($C_{16+}$-olefins). Isononyl alcohols which are used in large amounts as plasticizer alcohols can be obtained from the dibutenes by hydroformylation, hydrogenation and distillation. Isotridecyl alcohols can be obtained from the tributenes by means of analogous reactions. Mixtures of high-purity paraffins can be obtained from the $C_{16+}$-fraction by hydrogenation to the paraffins.

In a particularly preferred embodiment of the invention, a combined removal of thioethers and 1-butene by distillation is carried out directly or indirectly after the thioetherification. In particular, this combined thioether and 1-butene removal takes place after a selective hydrogenation of butadiene. The combined removal of thioethers and 1-butene by distillation is preferably carried out in a side offtake column from the top of which 1-butene and optionally isobutane are taken off while the thioethers are obtained at the bottom of the side offtake column. Raffinate III, viz. a $C_4$-hydrocarbon mixture which has been largely freed of butadiene, isobutene and 1-butene is taken off from the side offtake and, for example, passed to an oligomerization. The advantage of a combined removal of thioethers and 1-butene in a side offtake column is that a side offtake column incurs lower capital costs than two individual columns.

If an MTBE synthesis is provided after the thioetherification, it is possible to separate off the methyl tert-butyl ether (MTBE) formed from isobutene and methanol together with the thioethers as an ether mixture by distillation. This preferred embodiment combines the isolation of MTBE by distillation and the removal of the thioethers in one step.

However, the two ethers are not separated off separately in a side offtake column but instead in a conventional distillation column at the bottom of which an ether mixture consisting essentially of MTBE and thioethers is obtained. Since the thioethers are formed to a lesser extent than MTBE, the ether mixture can more accurately be described as an MTBE contaminated with thioethers.

The expected contamination of the MTBE with thioethers is so low that the ether mixture can contribute to the fuel pool like a technical-grade MTBE. Separate separation of the ether mixture into thioethers and pure MTBE is therefore not necessary. For this reason, the separate removal of the thioethers is dispensed with because it can be carried out together with the MTBE isolation which is necessary in any case. The capital and operating costs of the plant are decreased thereby.

Figure 2:
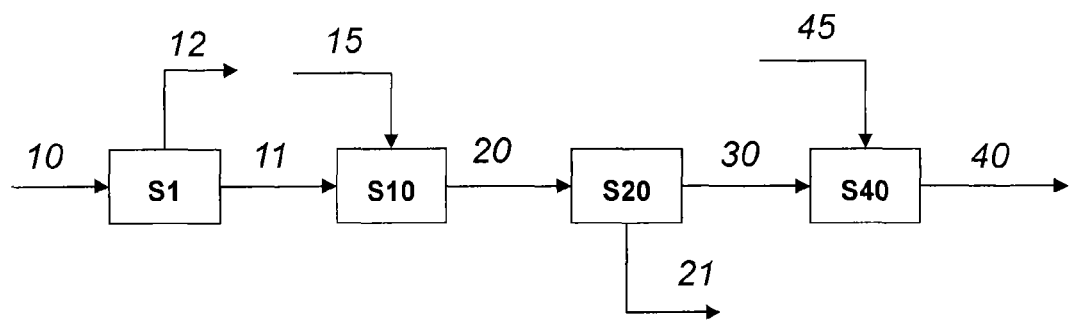
Figure 3:
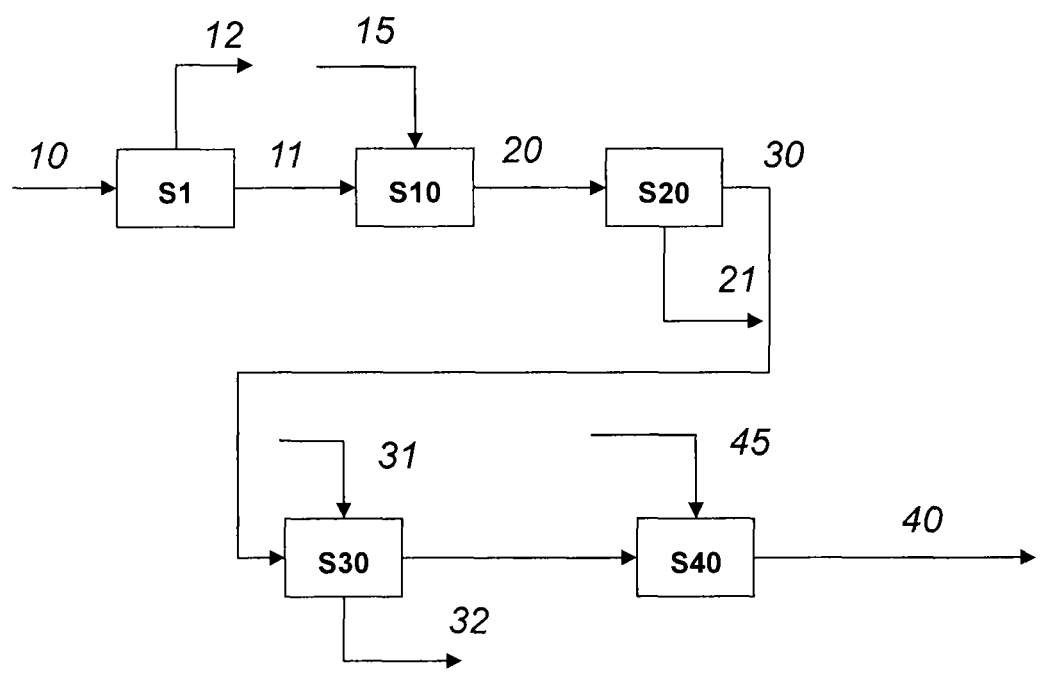
Figure 4:
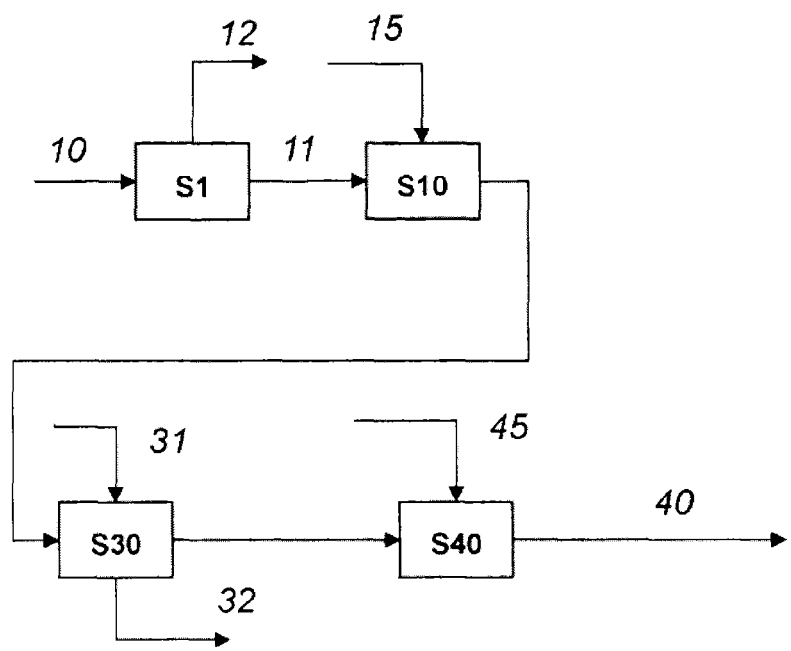
Figure 5:
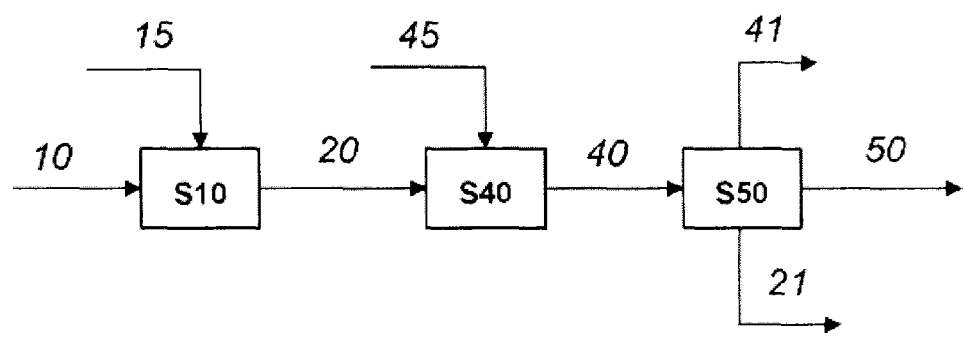

Some preferred embodiments of the present invention will now be illustrated with the aid of the figures. The figures show:

FIG. 1: Block diagram of a first embodiment;
FIG. 2: Block diagram of a second embodiment;
FIG. 3: Block diagram of a third embodiment;
FIG. 4: Block diagram of a fourth embodiment;
FIG. 5: Block diagram of a fifth embodiment.

A block diagram of a first preferred embodiment by means of which the process of the invention can be carried out is shown in FIG. 1. The mercaptan-containing $C_4$-hydrocarbon stream (10) is fed to the thioetherification step (S10). CO is optionally also fed to this step. Hydrogen (15) is also fed into the thioetherification step. In the thioetherification step, the mercaptans present are completely converted into thioethers, but 1,3-butadiene present is only partly converted.

The mercaptan-free stream (20) is fed to a distillation step (S20) in which the thioethers formed are separated off completely together with further relatively high-boiling components, e.g. $C_5$-hydrocarbons, as bottom stream (21). If no further high boilers are present, the thioethers can also be separated off later together with other high boilers formed in the sequence, e.g. MTBE. In the case of direct removal of high boilers (S20), the now sulphur-free overhead stream (30) is fed to a hydrogenation step (S40). In this hydrogenation step, 1,3-butadiene still present is selectively hydrogenated by means of hydrogen (45) to 1- and 2-butene. CO is optionally also fed to this step. The now sulphur- and 1,3-butadiene-free $C_4$-hydrocarbon stream (40) can now be used as raw material in further chemical production processes.

A second preferred embodiment of the process is shown in FIG. 2. In this process variant, low boilers (12), predominantly isobutane, are separated off from the $C_4$-hydrocarbon stream (10) in a first distillation step (S1). The further work-up of the largely low boiler-free stream (11) is carried out as described above for FIG. 1.

A third preferred embodiment of the process is shown in FIG. 3. In this process variant, the stream (30) after the high boiler removal (S20) is fed to an etherification stage (S30). In this stage, an alcohol (31), preferably methanol, is fed in and the isobutene obtained is converted into an ether, preferably methyl tert-butyl ether (MTBE). The ether is separated off as high boiler (32) and the isobutene-free stream (35) is fed to the hydrogenation step (S40) which has already been described above.

A fourth preferred embodiment of the process is shown in FIG. 4. As in the embodiment shown in FIG. 3, this process encompasses an MTBE synthesis (S30) arranged downstream of the thioetherification (S10). However, the thioethers are not discharged in a separate separation stage corresponding to the distillation step (S20) of the third embodiment but are instead discharged together with the MTBE as high-boiling ether mixture (32) from the etherification step (S30).

A fifth preferred embodiment of the process is shown in FIG. 5. The mercaptan-containing $C_4$-hydrocarbon stream (10) is fed to the thioetherification step (S10). CO is optionally also introduced into this step. Hydrogen (15) is also introduced into the thioetherification step. In the thioetherification step, the mercaptans present are completely converted into thioethers but 1,3-butadiene present is only partly reacted.

The mercaptan-free stream (20) is then fed to a hydrogenation step (S40). In this hydrogenation step, 1,3-butadiene still present is selectively hydrogenated by means of hydrogen (45) to 1- and 2-butene. CO is optionally also introduced into this step. The now mercaptan- and 1,3-butadiene-free $C_a$-hydrocarbon stream (40) is then fed into a side offtake column (S50) in which a combined removal of 1-butene and isobutane (41) via the top is effected. Raffinate III (50) is taken off from the side offtake. The thioethers 21 are taken off from the bottom of the side offtake column (S50). A combined removal of thioethers and 1-butene by distillation thus occurs in the side offtake column (50).

The present invention is illustrated below with the aid of examples. Alternative embodiments of the present invention can be obtained in an analogous way. The thioetherification is carried out in a fixed-bed reactor having a heating jacket through which a heat transfer oil (Marlotherm SH from Sasol Olefins & Surfactants GmbH) flows. As catalyst, use is made of 0.54 liter of a coated catalyst comprising 0.5% of palladium on γ-aluminium oxide in extrudate form. The catalyst is the NOBLYST® H1427-1 which can be obtained from Evonik Industries AG.

The specific internal surface area of the catalyst is about 250 $m^2$/g and the pore volume is about 0.8 $cm^3$/g. The thickness of the palladium layer is about 0.05 mm. To produce the thioetherified mixture of $C_a$-hydrocarbons, raffinate III, 1,3-butadiene and ethanethiol are mixed. Starting mixture and product mixture are analysed by gas chromatography.

EXAMPLE 1

According to the Invention

| Component | 1,3-Butadiene | 1-Butene | 2-Butenes | n-Butane | Ethanethiol |
|---|---|---|---|---|---|
| Feed [% by weight] | 0.513 | 27.710 | 44.987 | 26.292 | 0.00210 |
| Output [% by weight] | 0.345 | 27.552 | 45.325 | 26.284 | 0.00000 |

Reaction Conditions

| T [° C.] | P [bar] | Ratio of $N(H_2)/n$(diene) | Isomerization of 1-Butene [%] |
|---|---|---|---|
| 91 | 24 | 0.30 | 0.57 |

EXAMPLE 2

Comparative Example

| Component | 1,3-Butadiene | 1-Butene | 2-Butenes | n-Butane | Ethanethiol |
|---|---|---|---|---|---|
| Feed [% by weight] | 0.485 | 26.220 | 45.182 | 27.652 | 0.00200 |
| Output [% by weight] | 0.0 | 14.454 | 56.943 | 28.153 | 0.00010 |

Reaction Conditions

| T [° C.] | P [bar] | Ratio of $n(H_2)/n$(diene) | Isomerization of 1-Butene [%] |
|---|---|---|---|
| 96 | 24 | 2.06 | 44.87 |

EXAMPLE 3

According to the Invention

| Component | 1,3-Butadiene | 1-Butene | 2-Butenes | n-Butane | Ethanethiol |
|---|---|---|---|---|---|
| Feed [% by weight] | 0.502 | 29.489 | 46.949 | 22.502 | 0.00210 |
| Output [% by weight] | 0.325 | 29.276 | 47.381 | 22.461 | 0.00000 |

Reaction Conditions

| T [° C.] | P [bar] | Ratio of n(H$_2$)/n(diene) | Isomerization of 1-Butene [%] |
|---|---|---|---|
| 122 | 24 | 0.30 | 0.75 |

EXAMPLE 4

According to the Invention

| Component | 1,3-Butadiene | 1-Butene | 2-Butenes | n-Butane | Ethanethiol |
|---|---|---|---|---|---|
| Feed [% by weight] | 0.185 | 26.140 | 45.398 | 27.808 | 0.00200 |
| Output [% by weight] | 0.111 | 25.867 | 45.787 | 27.766 | 0.00000 |

Reaction Conditions

| T [° C.] | P [bar] | Ratio of N(H$_2$)/n(diene) | Isomerization of 1-Butene [%] |
|---|---|---|---|
| 118 | 24 | 0.54 | 1.04 |

EXAMPLE 5

According to the Invention

| Component | 1,3-Butadiene | 1-Butene | 2-Butenes | n-Butane | Methanethiol |
|---|---|---|---|---|---|
| Feed [% by weight] | 0.509 | 31.570 | 43.547 | 23.874 | 0.00207 |
| Output [% by weight] | 0.386 | 31.349 | 43.899 | 23.868 | 0.00000 |

Reaction Conditions

| T [° C.] | P [bar] | Ratio of n(H$_2$)/n(diene) | Isomerization of 1-Butene [%] |
|---|---|---|---|
| 105 | 24 | 0.29 | 0.70 |

EXAMPLE 6

Comparative Example

| Component | 1,3-Butadiene | 1-Butene | 2-Butenes | n-Butane | Ethanethiol |
|---|---|---|---|---|---|
| Feed [% by weight] | 0.506 | 38.882 | 39.693 | 20.414 | 0.00200 |
| Output [% by weight] | 0.508 | 38.897 | 39.700 | 20.392 | 0.00199 |

Reaction Conditions

| T [° C.] | P [bar] | Ratio of n(H$_2$)/n(diene) | Isomerization of 1-Butene [%] |
|---|---|---|---|
| 88 | 20 | 0.00 | −0.04 |

The tables of examples in each case show the significant composition of the feed stream and of the output stream of the fixed-bed reactor under various reaction conditions (without impurities).

In Example 1, the results of the thioetherification of about 5000 ppm of 1,3-butadiene and about 21 ppm of ethanethiol at an amount of hydrogen according to the invention are shown. It can be seen that ethanethiol can be etherified to a proportion by mass of 0 ppm without large amounts of the product of value 1-butene being lost. 1-Butene is reacted to an extent of only 0.59% (conversion=$(m_{in}-m_{out})/m_{in}$).

In Example 2, an excess of hydrogen over 1,3-butadiene of 2 (mol/mol) analogous to U.S. Pat. No. 5,851,383 is set. Here too, about 5000 ppm of 1,3-butadiene and about 20 ppm of ethanethiol are present in the feed. However, at this large amount of hydrogen, the proportion by mass of ethanethiol is reduced only to a value of about 1.0 ppm, which is not acceptable in the fine purification of C$_4$ fractions. In addition, the 1-butene content drops by more than 44%, while the n-butane content increases by 5000 ppm as a sign of total hydrogenation.

In Example 3, the temperature is increased to 122° C. Here too, at about 5000 ppm of 1,3-butadiene, about 21 ppm of ethanethiol can be thioetherified to a proportion by mass of 0 ppm without large proportions of the products of value being lost. 1-Butene is converted into 2-butenes to an extent of only 0.75%, while the proportion of butanes as a sign of total hydrogenation does not increase.

In Example 4, the feed concentration of 1,3-butadiene is reduced to about 1000 ppm and at the same time the ratio of hydrogen to diene is increased from 0.30 to 0.54. Here too, about 20 ppm of ethanethiol can be etherified to a proportion by mass of 0 ppm without large proportions of the products of value being lost. Due to the increased hydrogen/diene ratio, 1.04% of 1-butene are now reacted, but this is still a very low value. However, total hydrogenation to butanes does not take place.

Example 5 shows the results of the thioetherification of about 5000 ppm of 1,3-butadiene and about 21 ppm of methanethiol at an amount of hydrogen according to the invention. It can be seen that methanethiol, too, can be etherified to a proportion by mass of 0 ppm without large amounts of the product of value 1-butene being lost. 1-Butene is reacted to an extent of only 0.70%.

In Example 6, the reaction is carried out without hydrogen in the C$_4$-hydrocarbon stream. Here too, about 5000 ppm of 1,3-butadiene and about 20 ppm of ethanethiol are present in the feed. Without hydrogen, the proportion by mass of ethanethiol is not influenced, i.e. thioetherification does not take place without introduction of hydrogen.

Finally, the basic concept of the invention and their important uses will be summarized once more:

$C_4$-hydrocarbon streams contaminated with mercaptans, which usually originate from catalytic crackers, are unsuitable for oligomerization since the mercaptans seriously damage the oligomerization catalyst. Hitherto, such streams were freed of mercaptans in a costly MEROX® process, but the removal of the mercaptans was incomplete. This required removal of the remaining mercaptans by adsorption before the oligomerization. The fundamental concept underlying the invention is to etherify all mercaptans present in the $C_4$ stream to a higher molecular weight in order to make it possible to separate off the resulting thioethers by distillation. It has surprisingly been found that the thioetherification can be carried out over a heterogeneous catalyst when a very small amount of hydrogen is present. A great advantage of this process is that, owing to the low proportion of hydrogen, 1-butene present in the $C_4$ stream is barely isomerized and is also available as product of value, and also total hydrogenation to butanes does not take place. In addition, the process makes a costly MEROX® scrub dispensable.

The invention claimed is:

1. A process for removing mercaptans from a C4 hydrocarbon mixture, the C4 hydrocarbon mixture, comprising:
   1-butene, a multiply unsaturated hydrocarbon and a mercaptan;
   the process comprising:
   feeding the C4 hydrocarbon mixture to a reactor comprising a heterogeneous catalyst;
   feeding hydrogen to the reactor;
   reacting the mercaptan with the multiply unsaturated hydrocarbon in the presence of the hydrogen in a liquid phase in the presence of the heterogeneous catalyst to obtain a thioether; and
   separating the thioether from the C4 hydrocarbon mixture by distillation;
   wherein
   a molar ratio of the hydrogen to the multiply unsaturated hydrocarbon is from 1/100 to 8/10.

2. The process of claim 1, wherein the molar ratio of the hydrogen to the multiply unsaturated hydrocarbons is in a range from 1/10 to 5/10.

3. The process of claim 1, wherein the multiply unsaturated hydrocarbon is a compound selected from the group consisting of 1,3-butadiene, but-3-en-1-yne and 1,2-butadiene.

4. The process of claim 1, wherein the mercaptan is at least one of ethanethiol and methanethiol.

5. The process of claim 1, further comprising feeding carbon monoxide to the reactor, wherein a content of carbon monoxide fed to the reactor is less than 20 ppm, based on the mass of the C4 hydrocarbon mixture.

6. The process of claim 1, wherein the heterogeneous catalyst comprises a metal of group VIII of the Periodic Table of the Elements.

7. The process of claim 1, wherein the heterogeneous catalyst is a coated catalyst comprising aluminum oxide as a support and palladium as a catalytically active metal.

8. The process of claim 1, wherein an entry temperature of feed into the reactor is in the range from 0° C. to 180° C.

9. The process of claim 1, operated as a liquid-phase process in such a way that the hydrogen is completely dissolved in the liquid phase.

10. The process of claim 1, further comprising distilling the C4 hydrocarbon mixture for removal of low boilers prior to removal of the mercaptans.

11. The process of claim 1, further comprising, after the reacting, at least one operation selected from the group consisting of:
    removal of the thioether by distillation;
    removal of a sulfur component by adsorption;
    selective hydrogenation of 1,3-butadiene to 1-butene and/or 2-butene;
    removal of 1-butene by distillation;
    oligomerization of 2-butenes to form olefins having more than 4 carbon atoms;
    removal of n-butane and/or of isobutane by distillation; and
    etherification of isobutene with methanol to form methyl tert-butyl ether (MTBE) and removal of the MTBE formed.

12. The process of claim 11, comprising a combined removal of the thioether and 1-butene by distillation after the reacting.

13. The process of claim 11, where an etherification of isobutene by methanol to form methyl tert-butyl ether (MTBE) follows the thioetherification, and an ether mixture comprising MTBE and the thioether is subsequently separated off by distillation.

14. The process of claim 1, wherein an entry temperature of feed into the reactor is in the range from 60° C. to 150° C.

15. The process of claim 1, wherein an entry temperature of feed into the reactor is in the range from 80° C. to 130° C.

* * * * *